(12) United States Patent
Koest et al.

(10) Patent No.: US 6,409,346 B1
(45) Date of Patent: Jun. 25, 2002

(54) SLIT PROJECTOR

(75) Inventors: Gert Koest, Hannover; Marc Repnow, Bremen, both of (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 116 days.

(21) Appl. No.: 09/626,320

(22) Filed: Jul. 26, 2000

(30) Foreign Application Priority Data

Aug. 4, 1999 (DE) ......................................... 299 13 603

(51) Int. Cl.[7] .................................................. A61B 3/10
(52) U.S. Cl. ....................................................... 351/214
(58) Field of Search .............................. 351/205, 206, 351/207, 214, 215, 221; 359/362, 784

(56) References Cited

U.S. PATENT DOCUMENTS

| 4,699,482 A | | 10/1987 | Utsugi |
| 5,442,487 A | * | 8/1995 | Mizuno ...................... 359/784 |

FOREIGN PATENT DOCUMENTS

| WO | 99/12467 | 3/1999 |
| WO | 00/33729 | 6/2000 |

OTHER PUBLICATIONS

"The Multi–Purpose Camera: A New Anterior Eye Segment Analysis System", K. Sasaki, Y. Sakamoto, T. Shibata and Y. Emori May 1, 1990, pp. 3–8.
Book entitled "Ophthalmologisch–optische Intrumente" (translated Ophthalmologic Optic Instruments), published by Bernhard Rassow, pp. 99–119.

* cited by examiner

*Primary Examiner*—George Manuel
(74) *Attorney, Agent, or Firm*—Flynn, Thiel, Boutell & Tanis, P.C.

(57) ABSTRACT

The invention relates to a slit projector comprising a light source, a slit diaphragm arranged in front of the light source, and a lens system arranged in front of the slit diaphragm. Such a slit projector is used in particular in slit lamps. The front chamber of the eye can be illuminated with such slit projectors in order to be able, for example, to take pictures of the slit image of the front chamber of the eye. High performance light sources are needed for this. These are presently not available at acceptable prices. Therefore, the purpose exists to improve a slit projector in such a manner that same presents a slit of the needed brightness for viewing the eye and in particular for slit image photography. This is attained in such a manner that the light source consists of several light diodes 1 arranged essentially in a longitudinal direction of the slit, namely in the plane of the projected slit.

14 Claims, 2 Drawing Sheets

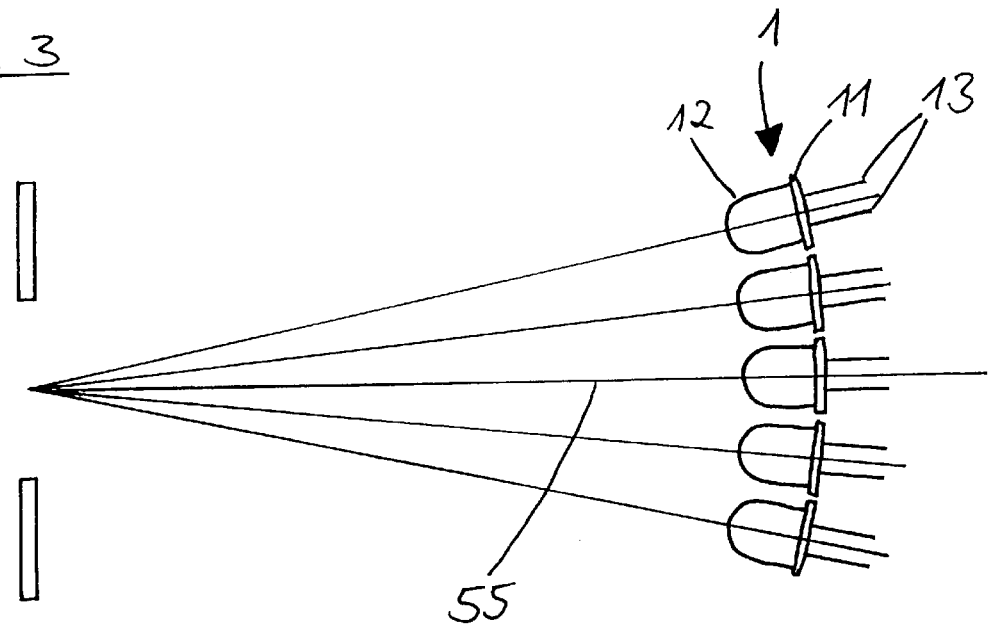
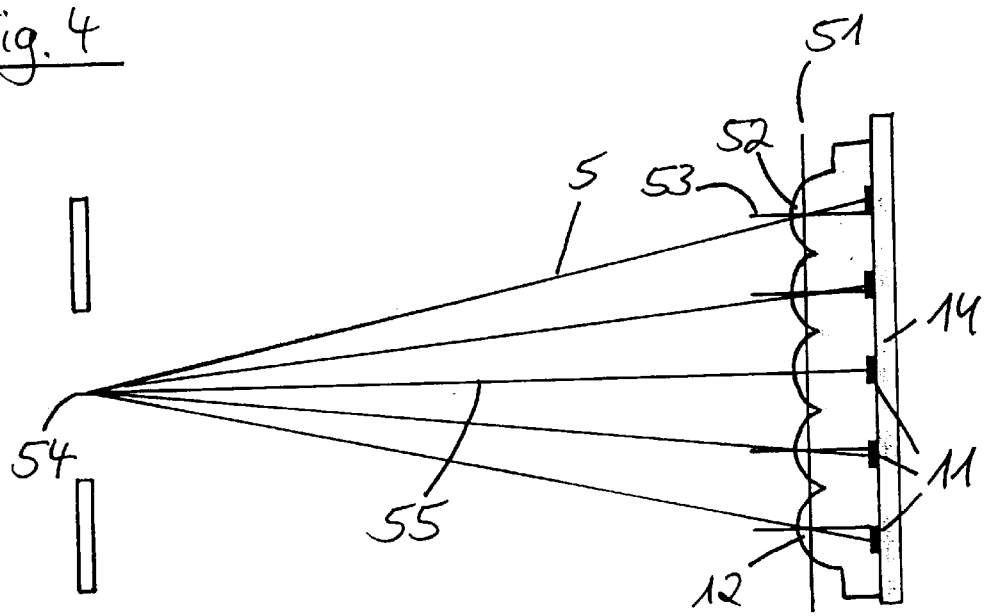

SLIT PROJECTOR

FIELD OF THE INVENTION

The invention relates to a slit projector comprising a light source of several light diodes arranged side-by-side and essentially in a longitudinal direction of the slit.

BACKGROUND OF THE INVENTION

Such a slit projector is known from the state of the art, for example, from the Book "Ophthalmologic Optic Instruments" published by Bernhard Rassow. The principle of the slit projector, as it is, for example, used in a slit lamp, is based on the fact that the refraction media of the front chamber of the eye are not highly transparent but instead a clear scattering occurs thereat in particular in the short-wave portion of the visible light. This has the result that a strongly concentrated light beam, which is sent through the optic media of the eye becomes, when viewed from the side, visible in the media similar to the beams of automotive headlights in fog. The various portions of the refraction media of the eye have a varying strong light scattering and can therefore be differentiated.

This principle of the focal illumination is perfected in the slit projector. A slitlike luminous beam of high brightness and a as high as possible color temperature (short-wave area) is used for the illumination.

A low voltage lamp has been successful in the past as the light source of such a slit projector because it enables a high light intensity with a relatively high color temperature. Halogen lamps have the advantage that they can tolerate higher stress during continuous operation and with this the color temperature increases clearly, furthermore their light is through holding only insignificantly changed. Only in a special design of a slit lamp with an extremely complicated construction there exists as the light source a Xenon high pressure lamp.

Ophthalmologists use slit projectors, with which besides the viewing of the front chamber of the eye also pictures of the transverse section or slit image of the front chamber of the eye can be taken. Good pictures of the front section of the eye require thereby a rather strong fading-out of the lens for shooting in order to achieve a good depth of sharpness. This means that the light sources must be very efficient regarding the illumination. Pictures of the front section of the eye in the optic section have up to now only been possible with an electronic flash or rather the Xenon high pressure lamp coupled into the slit illumination. In the case of the slit projector with a Xenon high pressure lamp we are dealing with a highly sophisticated and very expensive high quality device, which can be excellently utilized for complete diagnostic services and also for photography. However, this slit projector exceeds in its design and also in price by far the requirements set forth for the usual diagnostic services.

A further disadvantage when using common electronic flashes for the transverse section photography is the long charging duration of the electronic flash. Therefore, several seconds elapse always between the pictures until the electronic flash is ready again and a further picture can be taken. A total detection or scan of the front chamber of the eye by means of a photo slit lamp is therefore time consuming and expensive.

The basic purpose of the invention is therefore to provide a slit projector, which projects a slit of light to provide the necessary brightness for a viewing of the eye, and in particular also for the slit image photography, and enables a high image frequency.

This purpose is attained according to the invention in such a manner that the light source consists of several light diodes arranged essentially in a longitudinal direction of the slit, namely in the plane of the projected slit.

The inventive use of light diodes as the light source of the slit projector has several advantages. The advantage most important for the ophthalmologist is the high speed, with which the flashes needed for the slit image photography can be produced with the light diodes. Moreover light diodes are significantly compacter than the common light sources, the light diodes are more robust than the highly sensitive Xenon high pressure lamps and are noticeably less expensive.

The light diodes can then in a first embodiment according to the invention be arranged arclike or circularly lying in the plane of the projected slit. The curvature of the arc is then advantageously determined such that an as large as possible amount of light passes through the lens system.

The light diodes can in a different embodiment of the invention be arranged essentially in a plane parallel to the slit diaphragm. Main beams of the light diodes are then advantageously inclined relative to the optic axis of the lens system, and the inclination of the main beams is proportional to the distance of the light diodes from the optic axis of the lens system. The main beams of all light diodes intersect then advantageously essentially in one common point.

A slit light projection of the invention can advantageously have a second slit diaphragm in front of the lens system, whereby the slit of this second slit diaphragm is aligned with the slit of the first slit diaphragm.

The light fields can according to the invention consist of light diode chips. These light diode chips are then advantageously arranged along a straight line, whereby the connecting fields lie on both sides of the straight line. With this arrangement it is achieved that the areas of the light diode chips, which areas are uncovered by the connecting fields, lie as much as possible at the edge of the light fields reproduced on the first slit diaphragm and an as large as possible amount of light reaches the lens system.

In special embodiments it is possible for the diode lenses to be astigmatic and/or the lens system to consist of cylinder lenses. Both cases achieve a concentration of the light produced by the light fields on the slit in the first slit diaphragm.

This first slit diaphragm can according to the invention have a width of 50 to 120 $\mu$m, whereas the aperture angle of the beam concentration exiting from the first slit diaphragm is less than or equal to 2.9°.

In order to obtain an advantageous scattering behavior in the eye, light diodes, which produce blue light are preferred.

BRIEF DESCRIPTION OF THE DRAWINGS

The invention will be described in greater detail in connection with the drawings, in which:

FIG. 3 is a schematic illustration of the arrangement of the diodes of a slit beam projector according to FIGS. 1 and 2, and FIG. 4 is a schematic illustration of the arrangement of the light diodes in a different beam projector.

DETAILED DESCRIPTION

Figure 1:
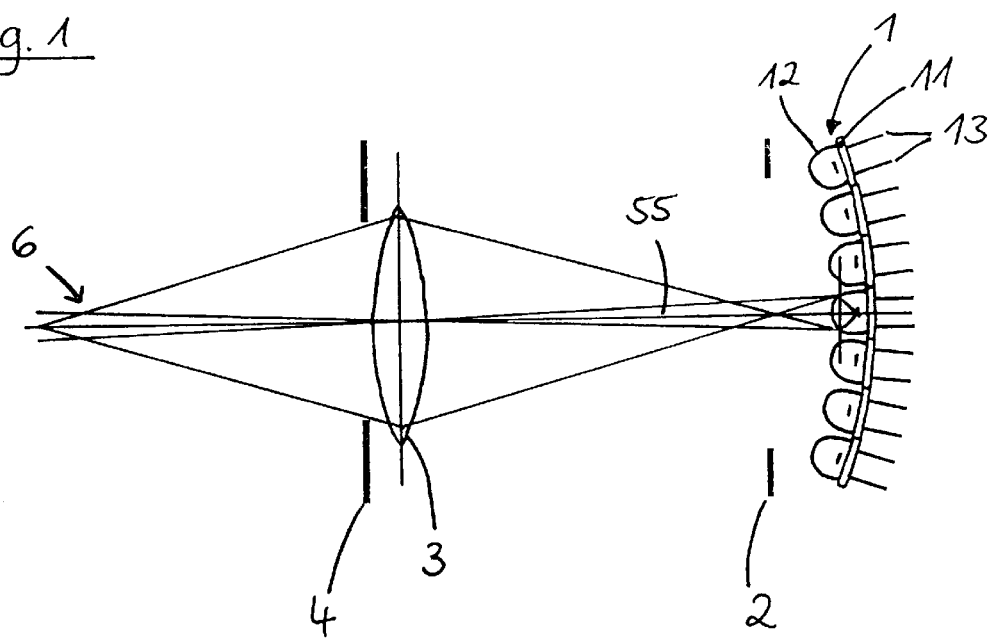
FIG. 1 is a schematic side view of a slit beam projector.
Figure 2:
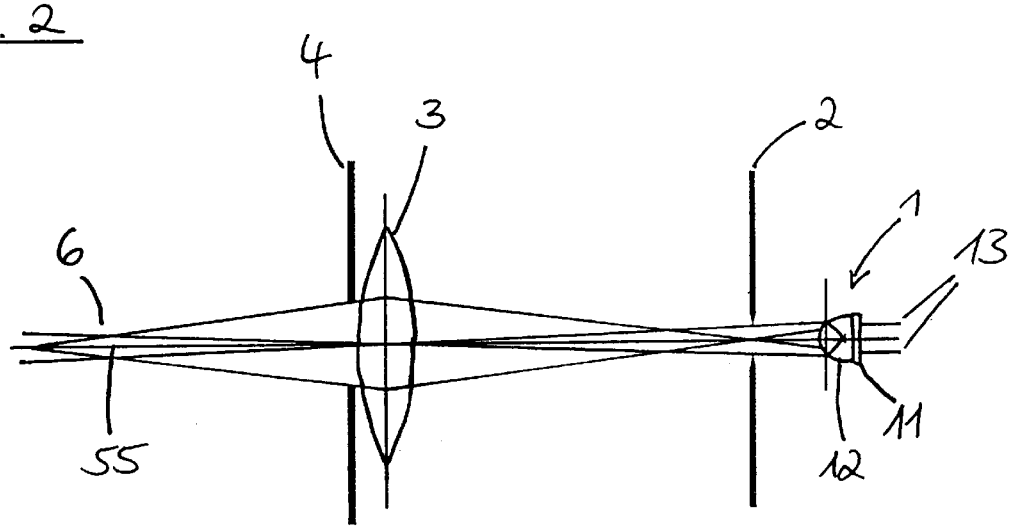
FIG. 2 is a top view of the slit beam projector according to FIG. 1.

Light diodes 1 are arranged on an arc in the exemplary embodiment of a slit beam projector schematically illustrated in FIGS. 1 and 2. The light diodes 1 illuminate a first slit diaphragm 2, in front of which a lens 3 is arranged. The curvature of the arc is thereby chosen such that as much light as possible enters through the lens 3. A further, second, slit diaphragm 4 is arranged in front of the lens 3, which slit diaphragm 4 results in a further concentration of the light beam.

FIG. 1 shows the beam path of the light diode, the main beam of which coincides with the optic axis 55 of the slit beam projector. FIG. 2 shows the same beam path in a horizontal cross section. The light fields of the light diode 1 are thereby shown according to the Koehler illumination principle known from the state of the art. The light field of the light diode 1 is thereby reproduced in the lens 3. The light field in turn reproduces the first slit diaphragm, which lies directly in front of the light diode 1 and is evenly illuminated, in the eye of the patient. Both in FIG. 1 and also in FIG. 2 one can recognize an area 6 of a significant concentration, in which area the light produced by the light diode 1 is concentrated as much as possible. The eye of the patient is advantageously located in this area 6 during the eye examination.

The light diodes 1 are arranged on an arc so that the main light beams from each light field thereof intersect in a common point. It is guaranteed in this manner that an as much as possible amount of light passes through the lens 3. The common point of intersection of the main beams lies thereby advantageously in the second slit diaphragm 4, in the lens 3 or between the second slit diaphragm 4 and the lens 3.

Another inventive arrangement (FIG. 4) of the light diodes 1 results also in a strong concentration of the light just like in the aforedescribed exemplary embodiment. The light fields 11 are in this arrangement of the light diodes 1 mounted along a straight line on a carrier bar 14. The diode lenses 12 are also mounted on a straight line in front of the light fields. The light fields 11 of the light diode 1 are thereby moved in the same direction relative to the diode lens 12 as the diode lens 12 is moved with respect to the optic axis 55 of the lens system or of the slit beam projector. The movement of the light field 11 is thereby proportional to the distance of the diode lenses 12 from the optic axis 55. The main beams 5 of all light diodes 1 intersect thereby in one common point 54. The main beams 5 are thereby the beams which, starting out from the centerpoint of a light field 11, pass through the point of intersection of the main plane 51 of the diode lens 12 and the optic axis 53 of the diode lens 52. With this arrangement of the diode lenses 12 and light fields 11 to one another it is achieved that the light fields 11 are reproduced in the lens 3 of the slit beam projector. Thus, in accordance with the Koehler illumination principle, an as large as possible concentration of the beams or an as large as possible brightness of the illuminated slit is achieved.

In contrast to the common light sources known from the state of the art, the light diodes have the advantage that they are significantly more robust and are easy to handle. A slit projector can be operated for a significantly longer time with light diodes than, for example, with Xenon high pressure lamps without the occurrence of breakdown. It is particularly advantageous in the case of light diodes that with light diodes a significantly lower heat development occurs so that a separate cooling of the light source is not necessary. Furthermore, slit projectors with light diodes are particularly well suited for slit image photography since a charging of capacitors to prepare the flash voltage is not necessary. In the case of the light diodes it is merely necessary to increase for the time of the photography the diode voltage, for example, to five times the value above the saturation value of the receptors of the eye. 80 to 100 ms, for example, lie between the individual photographs so that the flash sequence is increased at a multiple compared with a Xenon high pressure flash light.

What is claimed is:

1. A slit projector comprising a light source, a slit diaphragm arranged in front of the light source, and a lens system arranged in front of the slit diaphragm, in particular for slit lamps, wherein the light source consists of several light diodes arranged in a longitudinal direction of the slit, namely in the plane of the projected slit.

2. The slit projector according to claim 1, wherein the light diodes, lying in the plane of the projected slit, are arranged arclike or circularly.

3. The slit projector according to claim 2, the curvature of the arc is determined such that an as large as possible amount of light passes through the lens system.

4. The slit projector according to claim 1, the light diodes are arranged essentially in a plane parallel to the slit diaphragm.

5. The slit projector according to claim 4, the main beams of the light diodes are inclined relative to the optic axis of the lens system, and the inclination of the main beams is proportional to the distance of the light diodes from the optic axis of the lens system.

6. The slit projector according to claim 5, the main beams of all light diodes intersect essentially in one common point.

7. The slit projector according to claim 1, wherein a second slit diaphragm is arranged in front of the lens system, whereby the slit of said second slit diaphragm is coaxial and aligned with the slit of the first slit diaphragm.

8. The slit projector according to claim 1, the light fields of the light diodes consist of light diodes chips.

9. The slit projector according to claim 8, the light diode chips are arranged along a straight line, whereby their connecting fields lie on both sides of the straight line.

10. The slit projector according to claim 1, the diode lenses are astigmatic.

11. The slit projector according to claim 1, the lens system consists of cylinder lenses.

12. The slit projector according to claim 1, the slit of the first slit diaphragm has a width of 50 to 120 $\mu$m.

13. The slit projector according to claim 1, the aperture angle of the beam concentration exiting from the first slit diaphragm is less than or equal to 2.9°.

14. The slit projector according to claim 1, the light diodes produce blue light.

* * * * *